United States Patent
Zutshi et al.

(10) Patent No.: US 7,848,839 B2
(45) Date of Patent: Dec. 7, 2010

(54) SYSTEM, METHOD, AND MEDIUM FOR AN ENDPOINT DETECTION SCHEME FOR COPPER LOW-DIELECTRIC DAMASCENE STRUCTURES FOR IMPROVED DIELECTRIC AND COPPER LOSS

(75) Inventors: Ajoy Zutshi, Fremont, CA (US); Rahul Surana, Freemont, CA (US); Girish Dixit, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 398 days.

(21) Appl. No.: 12/004,730

(22) Filed: Dec. 21, 2007

(65) Prior Publication Data

US 2008/0109104 A1    May 8, 2008

Related U.S. Application Data

(63) Continuation of application No. 10/960,508, filed on Oct. 8, 2004, now abandoned.

(51) Int. Cl.
*G06F 19/00* (2006.01)
*G05B 15/00* (2006.01)

(52) U.S. Cl. ......................... 700/121; 700/83
(58) Field of Classification Search ............ 700/83, 700/121
See application file for complete search history.

(56) References Cited

U.S. PATENT DOCUMENTS

| | | | |
|---|---|---|---|
| 5,663,797 A | 9/1997 | Sandhu | |
| 5,667,424 A | 9/1997 | Pan | |
| 5,910,846 A | 6/1999 | Sandhu | |
| 5,961,369 A | 10/1999 | Bartels et al. | |

(Continued)

FOREIGN PATENT DOCUMENTS

JP    10034522 A    2/1998

(Continued)

OTHER PUBLICATIONS

Fang, S. J. et al, 1998, "Control of Dielectric Chemical Mechanical Polishing (CMP) Using an Interferometry Based Endpoint Sensor", International Proceedings of the IEEE Interconnect Technology Conference, pp. 76-78.

(Continued)

*Primary Examiner*—Ryan A Jarrett
(74) *Attorney, Agent, or Firm*—Blakely Sokoloff Taylor & Zafman LLP (57) ABSTRACT

A system, method and medium of detecting a transition interface between a first dielectric material and an adjacent second dielectric material in a semiconductor wafer during a chemical-mechanical polishing process includes impinging an incident light of a predetermined wavelength on the semiconductor wafer at a first time, detecting at least one first intensity of at least one first reflected light, impinging the incident light of the predetermined wavelength on the semiconductor wafer at a second time, detecting at least one second intensity of at least one second reflected light, and determining a difference between the at least one first intensity and the at least one second intensity. If the difference between the at least one first intensity and the at least one second intensity is above a predetermined threshold, the chemical-mechanical polishing process is terminated.

23 Claims, 6 Drawing Sheets

U.S. PATENT DOCUMENTS

| | | | |
|---|---|---|---|
| 6,108,092 | A | 8/2000 | Sandhu |
| 6,172,756 | B1 | 1/2001 | Chalmers et al. |
| 6,191,864 | B1 | 2/2001 | Sandhu |
| 6,214,734 | B1 | 4/2001 | Bothra et al. |
| 6,287,879 | B1 | 9/2001 | Gonzales et al. |
| 6,307,628 | B1 | 10/2001 | Lu et al. |
| 6,336,841 | B1 | 1/2002 | Chang |
| 6,503,839 | B2 | 1/2003 | Gonzales et al. |
| 6,517,413 | B1 | 2/2003 | Hu et al. |
| 6,652,355 | B2 | 11/2003 | Wiswesser et al. |
| 2002/0127950 | A1 | 9/2002 | Hirose et al. |
| 2003/0136663 | A1* | 7/2003 | Smith et al. ............ 204/192.13 |
| 2004/0018647 | A1* | 1/2004 | Jones et al. .................... 438/8 |

FOREIGN PATENT DOCUMENTS

| | | |
|---|---|---|
| JP | 200183001 A | 6/2000 |
| JP | 2001284299 A | 10/2001 |
| JP | 2002009030 A | 1/2002 |
| JP | 2002343754 A | 11/2002 |
| TW | 0434103 B | 5/2001 |
| TW | 0436383 B | 5/2001 |
| TW | 0455938 B | 9/2001 |
| TW | 0455976 B | 9/2001 |
| WO | WO 98/05066 | 2/1998 |
| WO | WO 99/09371 | 2/1999 |
| WO | WO 02/074497 A2 | 9/2002 |

OTHER PUBLICATIONS

Boning, Duane et al. "Run by Run Control of Chemical-Mechanical Polishing." IEEE Trans. Oct. 1996. vol. 19, No. 4, pp. 307-314.

Moyne, James et al. "A Run-to-Run Control Framework for VLSI Manufacturing." Microelectronic Processing '03 Conference Proceedings, Sep. 1993.

Telfeyan, Roland et al. "Demonstration of a Process-Independent Run-to-Run Controller." 187th Meeting of the Electrochemical Society, May 1995.

Moyne, James et al. "A Process-Independent Run-to-Run Controller and Its Application to Chemical-Mechanical Planarization." SEMI/IEEE Adv. Semiconductor Manufacturing Conference, Aug. 15, 1995.

Moyne, James et al. Adaptive Extensions to a Multi-Branch Run-to-Run Controller for Plasma Etching. Journal of Vacuum Science and Technology, 1995.

Sachs, Emanuel et al. "Process Control System for VLSI Fabrication."

Chaudhry, Nauman et al. "Active Controller: Utilizing Active Databases for Implementing Multi-Step Control of Semiconductor Manufacturing." University of Michigan pp. 1-24.

Chaudhry, Nauman et al. "Designings Databases with Fuzzy Data and Rules for Application to Discrete Control." Univeristy of Michigan pp. 1-21.

Chaudhry, Nauman et al. "A Design Methodology for Databases with Uncertain Data." University of Michigan pp. 1-14.

Khan, Kareemullah et al. "Run-toRun Control of ITO Deposition Process" University og Michigan pp. 1-6.

Moyne, James et al. "Yield Improvement @ Contact Through Run-to-Run Control".

Kim, Jiyoun et al. "Gradient and Radial Uniformity Control of a CMP Process Utilizing a Pre-and Post-Measurement Strategy." University of Michigan.

* cited by examiner

SYSTEM, METHOD, AND MEDIUM FOR AN ENDPOINT DETECTION SCHEME FOR COPPER LOW-DIELECTRIC DAMASCENE STRUCTURES FOR IMPROVED DIELECTRIC AND COPPER LOSS

RELATED APPLICATION

This application is a continuation of U.S. patent application Ser. No. 10/960,508, now abandoned, filed Oct. 8, 2004.

FIELD OF THE INVENTION

The present invention relates generally to control of chemical-mechanical polishing processes and more particularly to a system, method, and medium to detect an endpoint between two dielectric films to control the overall dielectric loss and metal loss in a polishing process, particularly a copper chemical-mechanical polishing damascene process.

BACKGROUND OF THE RELATED ART

Semiconductor manufacture is becoming an increasingly automated process requiring precise methods of process control to ensure a quality output. A wafer of a semiconductor chip is typically manufactured by etching the desired pattern in a low-dielectric constant ("Low-K") film and then filling the etched line, or trench, with first a thin layer of barrier material, typically 100 angstroms thick. The remainder of the trench is then filled with a conductive material, such as copper. In order to insure that all of the lines are uniformly filled, the line and the field area (i.e., the surface of the semiconductor wafer) are filled/covered with more barrier material and copper than is necessary, which leaves an excess of barrier material and copper on the surface of the Low-K film. Typical excess may consist of a 250 angstrom thick layer of barrier topped with an 8000 angstrom thick layer of copper.

Semiconductor chips are commonly fabricated from multiple stacked layers of materials on a semiconductor wafer. In small devices, for example 130 nm, 90 nm, and/or 65 nm devices, a thin dielectric anti-reflective coating ("DARC") layer, typically 500-600 angstroms, is deposited on top of the Low-K film between each successive layer. More specifically, the DARC layer is deposited directly on the field area of the semiconductor wafer, etched, and is then covered with barrier and copper. The DARC layer helps to reduce reflections from the reflection of light from metal, e.g., copper, embedded in the previous level of the semiconductor wafer.

For example, while performing a lithography patterning process on one level of wafer, whereby the etch pattern for the wafer is imprinted on the wafer, reflection from the copper in the preceding level of wafer can cause interference with the lithography tool. The lithography tool determines when lithography patterning on a portion of the wafer is completed by analyzing the light reflecting from that portion of the wafer. Reflected light from a previous level of wafer may convince the lithography tool that it has finished patterning that portion of the current wafer before the process has actually finished. Consequently, the DARC layer helps to minimize such interference and, thus, facilitate the lithography step.

One of the subsequent steps in a typical process involving copper is then to polish off the barrier material and copper and to then continue polishing off the DARC layer using a polishing, e.g., chemical-mechanical polishing (CMP) process. Ideally, the polishing process must stop at the transition interface between the DARC and a second dielectric film, which is the Low-K film. The final thickness of the Low-K film after polishing is complete is an indication of how much copper or metal is remaining in the line (the Low-K film having been etched and filled with copper).

Polishing away too much of the Low-K film, and, hence, too much of the copper in the line, affects at least two properties of the semiconductor wafer. First, the thickness of the Low-K film, which is proportional to the amount of copper in the line, determines the resistance of the line, where the lower the resistance the faster the device. If too much copper is removed, the effective resistance increases. Secondly, the Low-K film thickness determines the interlayer capacitance, where the lower the interlayer capacitance, the faster the device. If too much of the Low-K film is removed from the line, the interlayer capacitance increases. Thus, removing too much of the Low-K film lowers the effective speed of the device for both of the aforementioned reasons.

Since the thickness of the Low-K film affects the performance of semiconductor wafer devices, it is desirable to precisely maintain the thickness of the Low-K film from wafer to wafer. The Low-K film thickness that is required to be maintained to preserve, for example, the speed of the device, actually is part of the chip design. If the appropriate thickness of the Low-K film, and, thus, the amount of copper in the line, is not attained, then the semiconductor device will not achieve the desired performance. Therefore, it is important to reach the target for the thickness for the Low-K film and the copper in the line, as per the design specifications of the semiconductor wafer.

One current method of determining an endpoint, or the point at which the polishing process should be terminated, is based on polish time, which is a timed process. In the timed process, it is empirically determined how much time is required to polish off the copper, the barrier, and DARC film. This time could be set at any value, for example, forty seconds, thirty seconds, etc. The desire is to polish off as little of the Low-K film as is possible. However, when a wafer is polished, all surfaces of the wafer are not polished uniformly. As a result, there is a gradient in the surface of the wafer. Therefore, to insure that no residues are left on the surface of the wafer, more of the wafer is polished than is necessary, resulting in the loss of some Low-K film.

Another problem with the timed approach is that any slight shift in the material property of the barrier, DARC film, and/or the Low-K film affects the polish removal rate, and thus the amount of material that is removed within the predetermined time interval. Another factor effecting a change in the polish removal rate is the lack of consistency in CMP processes in the consumables, for example, the slurry and/or the pad. In effect, any change in the polish removal rate can affect the amount of Low-K film removed during the polishing process and may lead to too little or too much of the Low-K film being removed.

What is desired is an endpoint detection scheme that enables the polish process to be terminated at the transition interface between the overlying material and the Low-K layer of a semiconductor wafer such that little material in the Low-K layer of the wafer is removed.

SUMMARY OF THE INVENTION

Embodiments of the present invention define a technique to detect the change in reflectivity between two dielectric materials, e.g., a dielectric anti-reflective coating ("DARC") film and a low-dielectric constant ("Low-K") film using light with an appropriate wavelength, or range of wavelengths, to define an endpoint once the DARC film is completely removed.

Incident light of the appropriate wavelength, or range of wavelengths, is impinged multiple times upon the wafer at a particular rate. The intensity of the reflected light may be tracked as a function of time and the difference between successive intensities is monitored. Once the difference between successive intensities reaches a certain designated threshold, this indicates that the transition interface between, for example, the DARC film and the Low-K film has been reached. The polishing process can then, for example, be terminated at the transition interface.

The intensity of the reflected light at various times may be represented, for example, by a graph. In this graphical representation, the slope of the curve is defined by the changing intensity of the reflected light and serves as an indication of the transition between the DARC film layer and the Low-K film layer. Once the slope of the curve indicates that the transition has occurred, the polishing process can be immediately terminated, thus causing less of the desired Low-K material to be lost.

Various advantages of the present invention are achieved in a system of detecting a transition interface between a first dielectric material and an adjacent second dielectric material in a semiconductor wafer during a polishing process. The system includes a polishing tool that executes the polishing process, the polishing process being executed to remove a first dielectric material and expose a second dielectric material of the semiconductor wafer. The system also includes a light source that generates incident light of at least one predetermined wavelength upon a surface of the semiconductor wafer, and a detector that detects at least one reflected light intensity from the surface of the second dielectric material. The system further includes a data processor, in communication with the detector, that analyzes the reflected light intensity to determine and produce a signal when the transition interface between the first dielectric and the second dielectric has been detected.

In another embodiment, a method of detecting a transition interface between a first dielectric material and an adjacent second dielectric material on a semiconductor wafer during a polishing process includes initiating the polishing process, the polishing process being implemented to remove the first dielectric material and expose the second dielectric material of the semiconductor wafer; The method also includes impinging an incident light of at least one predetermined wavelength on the semiconductor wafer and detecting at least one first intensity of said incident light reflected from the semiconductor wafer at a first time. In addition, the method includes detecting at least one second intensity of said incident light reflected from the semiconductor wafer at a second time, determining a difference between the at least one first intensity and the at least one second intensity, and providing a signal when the difference between the at least one first intensity and the at least one second intensity is above a predetermined threshold, wherein the signal indicates that the transition interface has been detected.

In another embodiment, a polishing method for detecting a transition interface between a first dielectric material and an adjacent second dielectric material in a semiconductor wafer during a polishing process includes executing the polishing process, the polishing process being executed to remove a first dielectric material and expose a second dielectric material of the semiconductor wafer, and generating incident light of at least one predetermined wavelength upon a surface of the semiconductor wafer. The method also includes detecting at least one reflected light intensity from the surface of the second dielectric material and analyzing the reflected light intensity to determine and produce a signal when the transition interface between the first dielectric and the second dielectric has been detected.

In another embodiment, a computer-readable medium of instructions for detecting a transition interface between a first dielectric and an adjacent second dielectric in a semiconductor wafer during a polishing process includes initiating the polishing process, the polishing process being implemented to remove the first dielectric material and expose the second dielectric material of the semiconductor wafer, impinging an incident light of at least one predetermined wavelength on the semiconductor wafer, detecting at least one first intensity of said incident light reflected from the semiconductor wafer at a first time, detecting at least one second intensity of said incident light reflected from the semiconductor wafer at a second time, determining a difference between the at least one first intensity and the at least one second intensity, and providing a signal when the difference between the at least one first intensity and the at least one second intensity is above a predetermined threshold, wherein the signal indicates that the transition interface has been detected.

Additional embodiments are also contemplated herein.

DETAILED DESCRIPTION

Reference now will be made in detail to various embodiments of the present invention. Such embodiments are provided by way of explanation of the invention and are not intended to be limited thereto. In fact, those of ordinary skill in the art may appreciate upon reading the present specification and viewing the present drawings that various modifications and variations can be made.

The end-point detection scheme of the present invention creates an endpoint system for a CMP process, for example, a copper damascene CMP process, which enables accurate detection of the transition interface between a DARC layer and a Low-K layer. By detecting this transition, a control system would be able to determine when to stop the CMP process such that a final thickness of the Low-K layer is consistent from wafer to wafer. This consistency is achieved because the transition interface can act as the sole indication of when the CMP process should be stopped. All other variables, for example, properties of the Low-K film, itself, properties of the consumables, etc., can be eliminated from concern.

Figure 1:
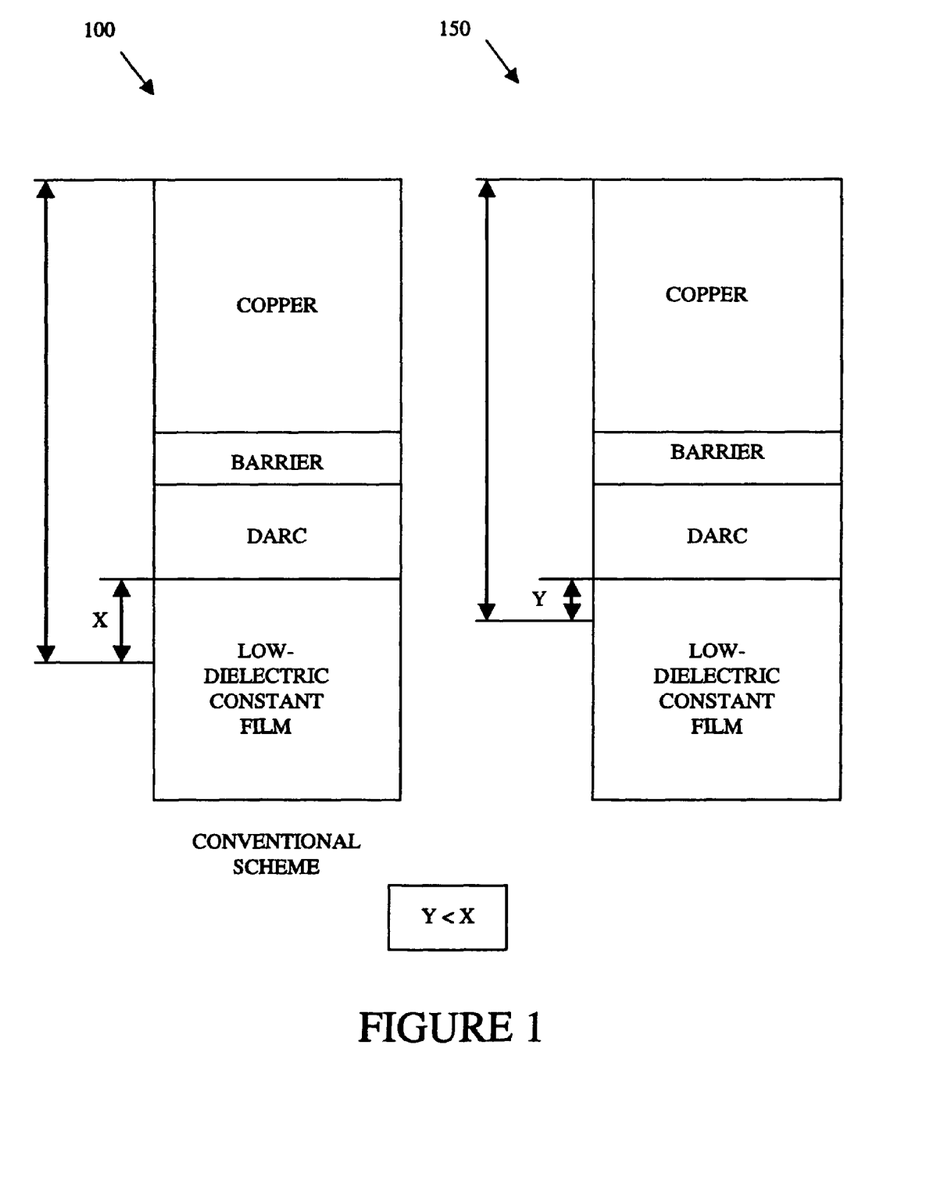
FIG. 1 illustrates a comparison between a prior art scheme for end-point detection and a scheme for end-point detection as contemplated by embodiments of the present invention.

FIG. 1 illustrates the advantage of an end-point detection scheme of the current invention over a conventional scheme. The goal of an end-point detection scheme is to remove the undesired material, for example, the DARC film layer, without removing too much of the Low-K layer. In conventional detection scheme 100, the variable "X" indicates the amount of Low-K material removed using, for example, timing as the sole indicator of when end-point has been achieved. In detection scheme 150, the variable "Y" indicates the amount of Low-K material removed using the detection of the transition between the DARC layer and the Low-K layer, as proposed by one or more embodiments of the present invention. As Y is less than X, it is shown in the comparison that less of the desired material in the Low-K layer is removed by using detection scheme 150 than by using prior art detection scheme 100.

Figure 2:
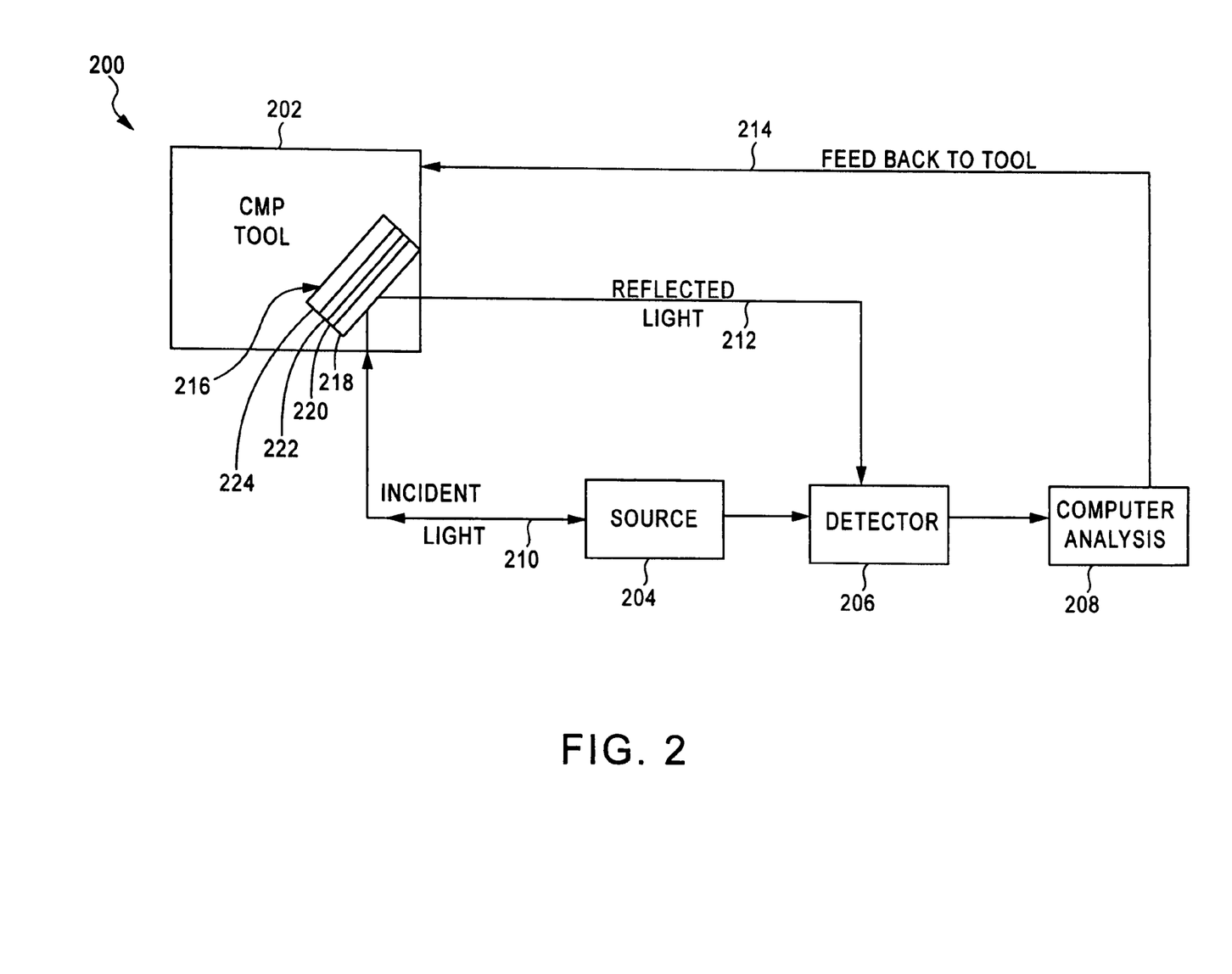
FIG. 2 is a block diagram illustrating a system related to the end-point detection scheme as contemplated by embodiments of the present invention.

FIG. 2 illustrates a system setting forth the end-point detection scheme as contemplated by embodiments of the present invention. System 200 includes, for example: CMP tool 202, incident light source 204, reflected light detector 206, and computer analysis system 208.

CMP tool 202 can be a piece of semiconductor manufacturing equipment that implements just the CMP function, or possibly one or more additional functions such as CVD, etching, and other such processes on a wafer 216. Examples of such tools are the Mirra™ and Mirramesa™ tools, as well as the Reflection™ tool, all of which are manufactured by Applied Materials.

Wafer 216 has, for example, copper 218, barrier 220, DARC layer 222, and Low-K layer 224. In at least one embodiment of the present invention, source 204 and detector 206 are integral with CMP tool 202, while computer analysis system 208 is remote from CMP tool 202. In an alternate embodiment, source 204 and/or detector 206 are also remote from CMP tool 202, along with computer analysis system 208. Furthermore, in another alternate embodiment, source 204, detector 206, CMP tool 202 and computer analysis system 208 are all integral with each other.

Source 204 produces incident light 210. Incident light 210 can be, for example, a coherent light of a single wavelength. For example, incident light 210 may have a wavelength of approximately 400 nm. In an alternate embodiment, incident light 210 is multi-wavelength light, e.g., "white light," of frequencies of approximately 400 nm to 900 nm. The techniques described below may be used with either type of incident light, although processing for multi-wavelength light needs to take into account the multiple wavelengths involved.

Particular materials will produce detectable intensities or reflectivity peaks only at specific wavelengths of incident light. Such specificity is an inherent property of the material and is dependent upon the atomic structure of the material. However, any impurities introduced into the material may alter the wavelength at which the reflectivity peaks for that material occur. Therefore, since most dielectric material will contain some impurities, to use white light as incident light 210, the specific wavelengths of light where detectable reflectivity peaks can be found must first be determined.

This determination can be performed by scanning the first dielectric material, for example, DARC layer 222, and the second dielectric material, for example, Low-K layer 224, and detecting which wavelengths of incident light 210 produce the most detectable reflectivity peaks of reflected light 212 for both dielectric materials. Computer analysis system 208 can then be programmed to monitor the reflected light 212 produced, e.g., only by those wavelengths. Thus, by using white light as incident light 210, the multiple reflectivity peaks can be used as a redundant, error-checking method.

For example, the condition can be set that the end-point of the polishing process is detected only when each reflectivity peak of the second dielectric has been detected (and the reflectivity peaks of the first dielectric are no longer detected). For DARC layer 222 and Low-K layer 224, there are typically three or four detectable reflectivity peaks. It should be understood, that light of various other frequencies (i.e., other than white light) can also be used as incident light 210, so long as the appropriate detectable peak reflected intensities can be generated.

Incident light 210 impinges upon a surface of wafer 216. For example, during the CMP process, incident light 210 impinges upon barrier 218. As the CMP process continues, barrier 218 and DARC layer 220 are removed from the surface of wafer 216, allowing incident light 210 to impinge on each material in turn.

Incident light 210 reflects from the surface of wafer 216 and reflected light 212 is intercepted by detector 206. Detector 206 detects an intensity of reflected light 212. The intensity of reflected light 218 will vary, depending on from which surface, barrier 218, DARC layer 220, or Low-K layer 222, reflected light 218 is reflected.

Detector 206 sends data indicating the intensity of reflected light 212 to computer analysis system 208. Computer analysis system 208 stores varying intensity of reflected light 212 over time and determines when the threshold has been reached between DARC layer 220 and Low-K layer 222 by tracking the change, or delta, in the intensity of reflected light 212. Once this delta has reached a predetermined threshold, as defined by e.g., a user, and/or determined based on the known reflectivities of DARC layer 220 and Low-K layer 222, computer analysis system 208 generates feedback signal 214. (It should thus be understood that the predetermined threshold could be set to indicate removal of either all or less than all of the DARC layer.)

Feedback signal 214 can be used to, for example, direct CMP tool 202 to halt the process currently being executed, for example, the polishing process. Additionally, feedback signal 214 can be used to help define process control charts for the polishing process. For instance, if a large number of wafers, for example, 50 to 100 wafers, were polished using the method of the present invention, data pertaining to the amount of time it takes to remove the DARC and residual barrier material and copper, and to reach the transition interface, can be collected. From this statistical information, the stability of the process can be determined and process controls for the polishing process can be better defined.

It should, of course, be understood that the present invention can also be used to detect a transition between other types of non-metallic materials in the course of semiconductor manufacture. In general, the process of the present invention can be used to detect a transition interface between any such dissimilar materials that show different transitions for absorption or reflection spectra. For example, in semiconductor manufacturing, the process can be used to detect a transition between a nitride film and an oxide film in a Shallow Trench Isolation process.

Figure 3:
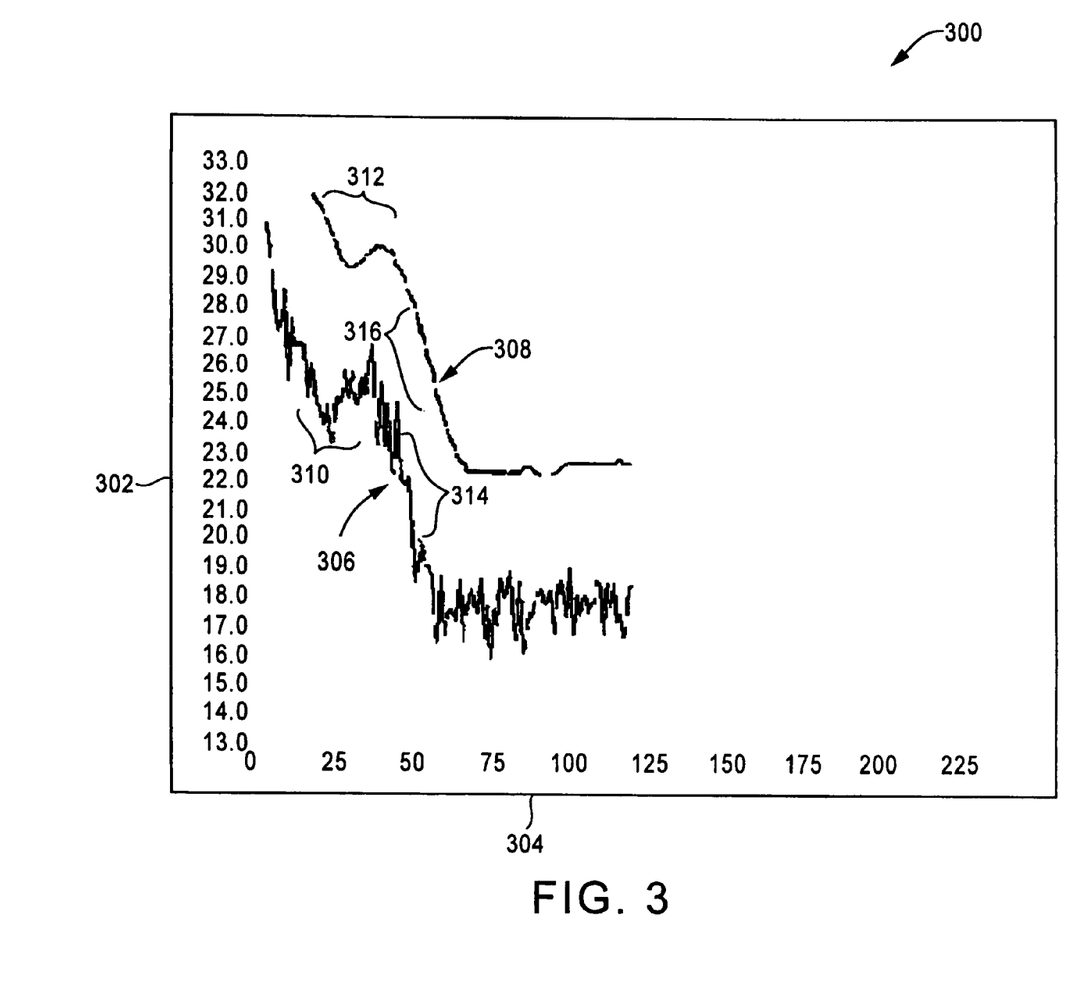
FIG. 3 is a graphical representation of a reflected light intensity being track over time.

FIG. 3 illustrates a graphical representation 300 of an example of intensity of reflected light 212 tracked over a period of time. Computer analysis system 208 can be instructed to provide this graphical output for a human observer. The intensity of reflected light 212 is represented by y-axis 302 in, for example, Lumens units. Time is represented by the x-axis 304 in, for example, seconds or milliseconds. Line graph 306 plots the intensity of reflected light 212 over a period of time. The intensity of reflected light 212 may be captured in varying time intervals, where the shorter the time interval, the more accurate the tracking of the change in the intensity. Averaged line graph 308 represents an average of line graph 306, allowing a human observer to more easily track the change in the intensity of reflected light 212. Graphical representation 300 may be displayed to a human operator using, for example, a display associated with computer analysis 208, or alternately, using some other method of display.

A substantial change in the slope of line graph 306, and as a result, averaged line graph 308, may indicate a transition between layers of material in wafer 216. For example, area 310 of line graph 206 and area 312 of averaged line graph 308 may indicate the transition between barrier 281 and DARC layer 220. Likewise, area 314 of line graph 306 and area 316 of averaged line graph 308 may indicate the transition between DARC layer 220 and Low-K layer 222. It should be noted that the slope of areas 310, 312 is different from the slope of area 314, 316. Only one of these slopes will be indicative of the predetermined change, or delta, in the intensity of reflected light 212 that signals that the transition interface between DARC layer 220 and Low-K layer 222 has been reach, and thus, that the end-point has been achieved. For example, the largest slope, which in FIG. 3 is the slope of area 314, 316, signals reflected light 212 is beginning to reflect from Low-K layer 222 rather than DARC layer 220. Computer analysis system 208 can, for example, then command CMP tool 202 to halt when the appropriate delta occurs.

In other (or overlapping) embodiments, a more precise determination of the slope of the graph can be obtained by programming computer analysis system 208 to take the derivative of line graph 306 and/or the derivative of averaged line graph 308. Taking the derivative yields precise, numerical values that represent the delta in the intensity of reflected light 212 at any given time. The derivative then also can be plotted against time, allowing a human operator to more accurately judge when the predetermined delta of the intensity of reflected light 212 occurs.

Figure 4:
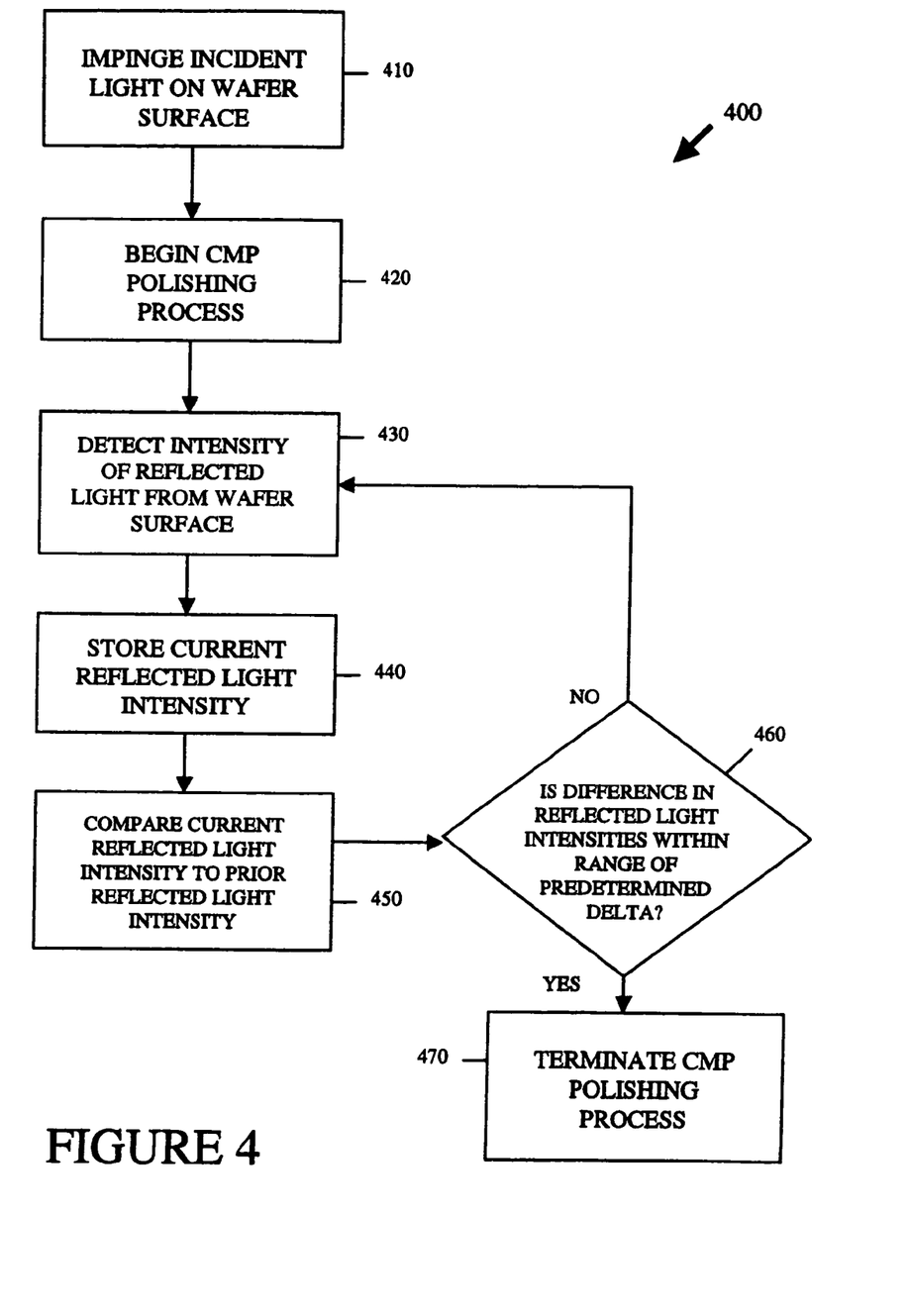
FIG. 4 is a flow chart illustrating a method of end-point detection according to embodiments of the present invention.

FIG. 4 is a flow chart illustrating a method of end-point detection. As described previously, incident light source 204 impinges onto the surface of wafer 216 with incident light 210 (step 410). CMP tool 202 then begins the CMP polishing process (step 420). It should be noted that CMP tool 202 alternately may begin the polishing process before or simultaneously with incident light 210 impinging on the surface of wafer 216.

Reflected light 212, which is then currently being reflected from the surface of wafer 216, is detected by reflected light detector 206 (step 430). The current reflected light intensity is stored, for example, in a memory within or otherwise associated with computer analysis system 208 (step 440). Computer analysis system 208 compares the current reflected light intensity to a prior reflected light intensity (step 450). If the current reflect light intensity is the first recorded data point, it may be simply stored without comparison or, alternately, it may be compared to some initial null value.

Computer analysis system 208 compares reflected light intensities by, for example, taking the difference between the reflected light intensities. Computer analysis system 208 thus calculates a delta, which represents this difference. Computer analysis system 208 then determines whether the delta is substantially equal to, or within an acceptable range of, the predetermined delta (step 460). As stated previously, the predetermined delta can be, for example, a user defined value, which signifies that the end-point has been achieved.

If the delta is not substantially equal to, or is not within the range of, the predetermined delta, the CMP polishing process continues, with a new reflected light intensity being detected from the surface of wafer 216 (step 430). As the polishing process continues, the surface of wafer 216 will change from, for example, barrier layer 218 to DARC layer 220, and finally, to Low-K layer 222. If the delta is substantially equal to, or is within range of, the predetermined delta, signifying that the end-point has been achieved, computer analysis system 208 sends feedback signal 214 to CMP tool 202 and instructs CMP tool 202 to terminate the CMP polishing process (step 470), and/or generates some other notification that the end-point has been reached. Regarding decision block 460 and the flow diagram of FIG. 4, generally, it should be understood that termination of the CMP process may also be triggered once a certain delta in intensity has been detected over more than just a single comparison of current versus previous intensity.

In addition to utilizing detection of the known peak intensities of the dielectric (e.g., low-K) to be uncovered by the polishing process for error-checking as indicated above, embodiments of the present invention also contemplate that the detection of the peak intensities, themselves, can serve as the determining factor for whether the polishing process is to be terminated.

Figure 5:
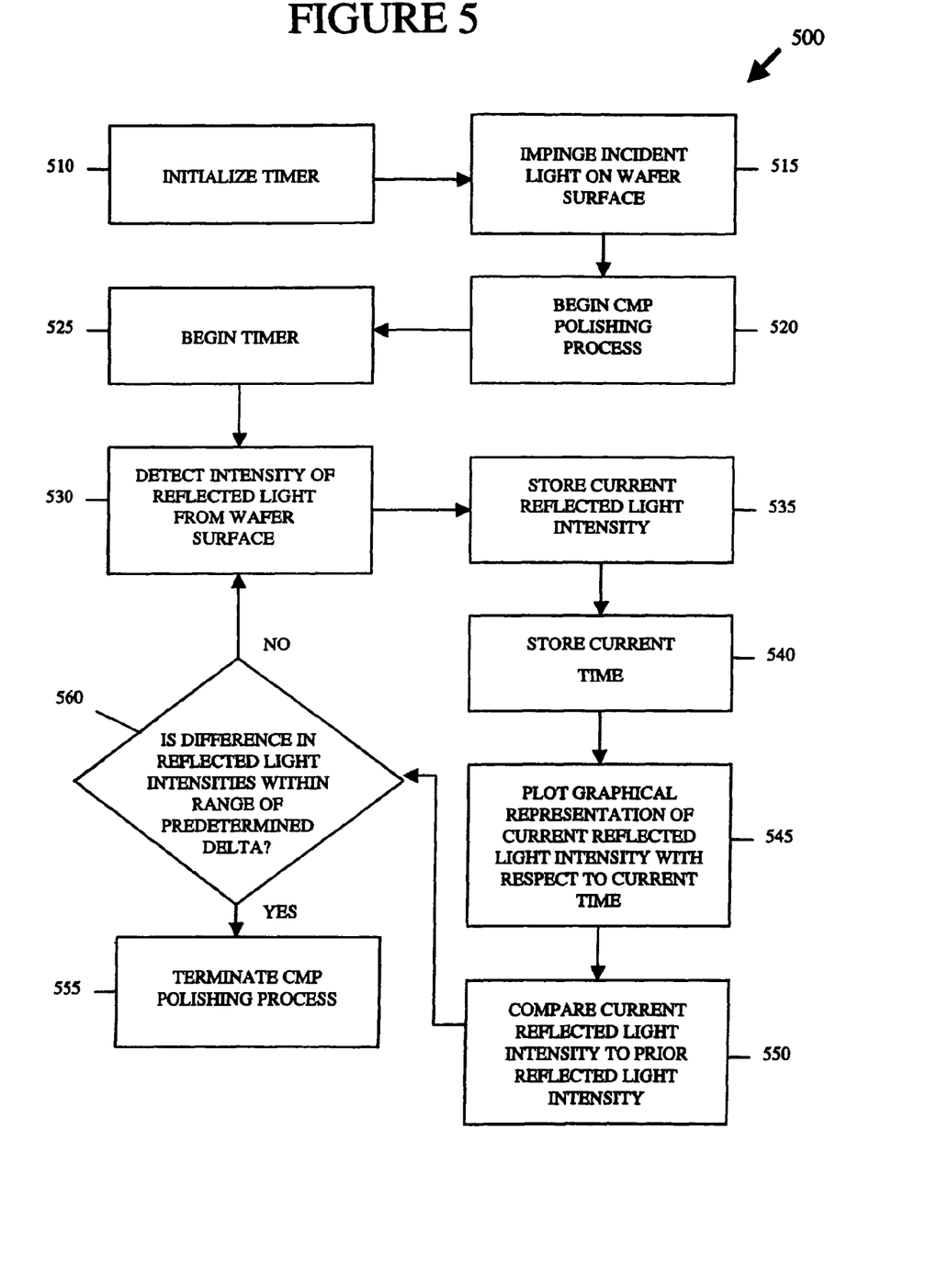
FIG. 5 is a flow chart illustrating an alternate method of end-point detection according to embodiments of the present invention.

FIG. 5 is a flow chart illustrating alternate (or overlapping) embodiments of a method of end-point detection. As described previously, a graphical representation of the intensity of reflected light 212 as a function of time may be used to more readily provide a visual indication to a human operator as to when the end-point has been achieved. The time is tracked, for example, from the start of the process. A timer is initialized by, for example, computer analysis tool 208 (step 510) such that time can commence from some initial value. The timer may be, for example, the internal clock of computer analysis system 208.

Incident light source 204 impinges incident light 210 on the surface of wafer 216 (step 515). CMP tool 202 then begins the CMP polishing process (step 520). As stated previously, the polishing process may commence either prior to or simultaneously with incident light 210 impinging on the surface of wafer 216. Timer 525 begins to run, for example, concurrently with the beginning of the polishing process (step 525).

The intensity of reflected light 212 at the then current time is detected by reflected light detector 206 (step 530). The value of the intensity is stored, for example, in a memory within or otherwise associated with computer analysis system 208 (step 535). Similarly, the then current time may also be stored (step 540). Using the stored intensity and time values, computer analysis system 208 can plot the intensity with respect to the then current time (step 545).

Computer analysis system 208 compares the current reflected light intensity to a prior reflected light intensity (step 550). If the current reflect light intensity is the first recorded data point, it may be simply stored without comparison or, alternately, it may be compared to some initial null value (as is also the case for the embodiments of FIG. 4). Computer analysis system may compare reflected light intensities as described previously, by calculating a delta. Alternately (or additionally), computer analysis system 208 may make use of the graphical plot of the reflected intensities and calculate, for example, a slope representing the change in the light intensities over time. Thus, computer analysis system can determine whether the delta is substantially equal to, or with range of, the predetermined delta, or alternatively, whether the slope of the graph is substantially equal to, or within range of, some predetermined slope that signal the transition interface between DARC layer 220 and Low-K layer 222 (step 560).

If the delta is not substantially equal to, or is not within the range of, the predetermined delta, or alternately, the slope of the graph is not substantially equal to, or is not within the range of, the predetermined slope, the CMP polishing process continues, with a new reflected light intensity being detected from the surface of wafer 216 (step 530). If the delta is substantially equal to, or is within range of, the predetermined delta, signifying that the end-point has been achieved, computer analysis system 208 sends feedback signal 214 to CMP tool 202 and instructs CMP tool 202 to terminate the CMP polishing process (step 555).

In other alternative (or overlapping) embodiments, the user may also define a particular time interval, or frequency of measurement, during which the slope of the graph reaches a certain value to signify that the end-point has been achieved. Thus, computer analysis system 208 takes into account two factors in determining whether to instruct CMP tool 202 to terminate the polishing process. This method is similar to the method depicted in FIG. 5, with the additional tracking of the predetermined time interval as well as the predetermined slope that signifies that the end-point has been achieved.

Figure 6:
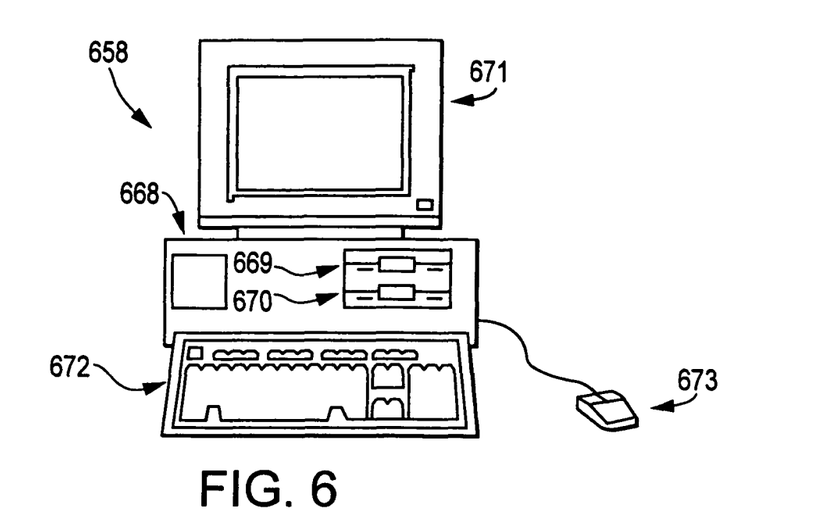
FIG. 6 is an illustration of a computer used for implementing the computer processing in accordance with computer-implemented embodiments of the present invention.

Various aspects of the present invention that can be controlled by a computer can be controlled by any number of control/computer entities, including the one shown in FIG. 6. FIG. 6 is an illustration of a computer 658 used for implementing the computer processing in accordance with computer-implemented embodiments of the present invention. The procedures described above may be presented in terms of program procedures executed on, for example, a computer or network of computers.

Viewed externally in FIG. 6, computer 658 has a central processing unit (CPU) 668 having disk drives 669, 670. Disk drives 669, 670 are merely symbolic of a number of disk drives or other storage units that might be accommodated by computer 658. Typically, these might be one or more of the following: a floppy disk drive 669, a hard disk drive (not shown), and a CD ROM or digital video disk, as indicated by the slot at 670. The number and type of drives varies, typically with different computer configurations.

Computer 658 also has a display 671 upon which information may be displayed. The display is optional for the computer used in conjunction with the system described herein. A keyboard 672 and/or a pointing device 673, such as a mouse 673, may be provided as input devices to interface with central processing unit 668. Other input devices are also contemplated.

Figure 7:
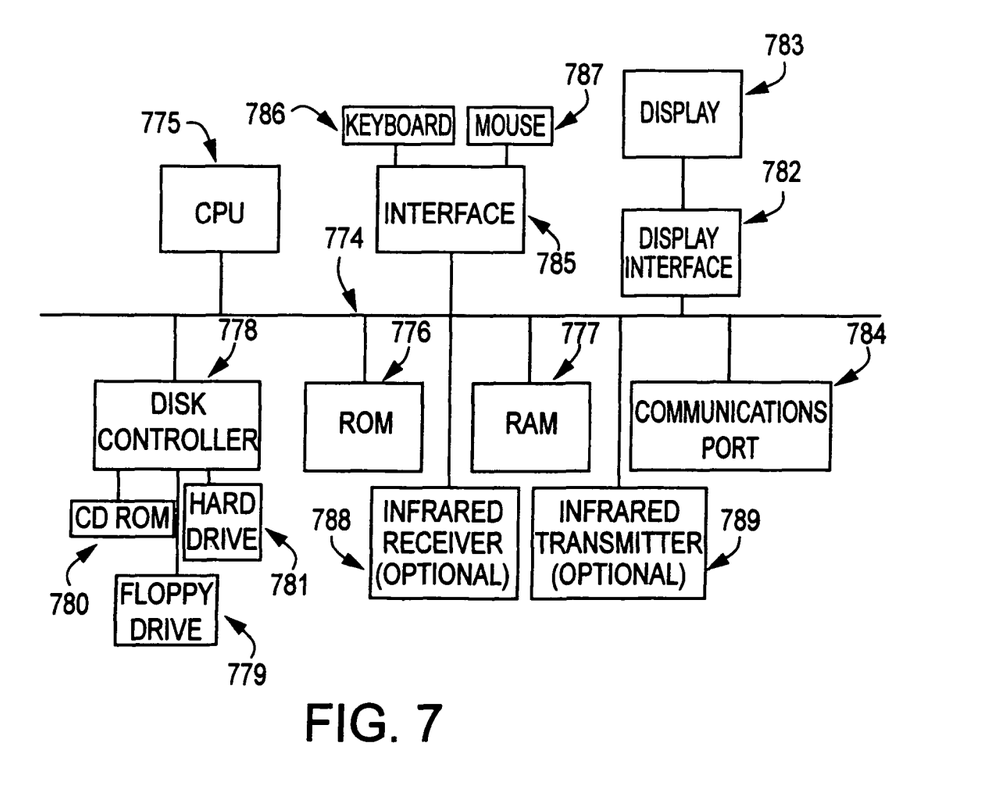
FIG. 7 illustrates a block diagram of the internal hardware of a computer.

FIG. 7 illustrates a block diagram of example internal hardware of the computer of FIG. 6. CPU 775 is the central processing unit of the system, performing calculations and logic operations required to execute a program. Read only memory (ROM) 776 and random access memory (RAM) 777 constitute the main memory of the computer. Disk controller 778 interfaces one or more disk drives to the system bus 774. These disk drives may be floppy disk drives such as 779, or CD ROM or DVD (digital video/versatile disk) drives, as at 780, or internal or external hard drives 781.

A display interface 782 permits information from bus 774 to be displayed on the display 783. The computer may also have an infrared receiver 788 and transmitter 789. Communication with external devices occurs using communications port 784.

In addition to the aforementioned components of the computer, the computer may also include an interface 785, which allows for data input through the keyboard 786 or pointing device, such as a mouse 787.

The foregoing detailed description includes many specific details. The inclusion of such detail is for the purpose of illustration only and should not be understood to limit the invention. In addition, features in one embodiment may be combined with features in other embodiments of the invention. Various changes may be made without departing from the scope of the invention as defined in the following claims.

As one example, the system according to the invention may include a general purpose computer, or a specially programmed special purpose computer. The user may interact with the system via e.g., a personal computer or over PDA, e.g., the Internet an Intranet, etc. Either of these may be implemented as a distributed computer system rather than a single computer. Similarly, the communications link may be a dedicated link, a modem over a POTS line, and/or any other method of communicating between computers and/or users. Moreover, the processing could be controlled by a software program on one or more computer systems or processors, or could even be partially or wholly implemented in hardware.

Any presently available or future developed computer software language and/or hardware components can be employed in such embodiments of the present invention. For example, at least some of the functionality mentioned above could be implemented using Visual Basic, C, C++ or any assembly language appropriate in view of the processor being used. It could also be written in an interpretive environment such as Java and transported to multiple destinations to various users. See also U.S. Pat. No. 6,652,355, which is incorporated by reference in its entirety.

It is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

What is claimed is:

1. A method, implemented by a computer analysis system programmed to perform the following, comprising:
    receiving, by the computer analysis system, a user input, wherein the user input defines a threshold to indicate a transition between a dielectric anti-reflective coating film layer and an adjacent low-k film layer;
    initializing, by the computer analysis system, a timer coupled to the computer analysis system for time to commence at an initial value corresponding to a time of a tool starting a process;
    receiving, by the computer analysis system, data from a detector coupled to the computer analysis system, the data comprising an intensity of at least one reflected light that is measured by the detector for at least two points in time;
    storing, by the computer analysis system, the data from the detector in memory coupled to the computer analysis system;
    plotting, by the computer analysis system, a graphical representation of the data as a function of time using the stored data;
    determining, by the computer analysis system, whether a slope calculated from the graphical representation meets the threshold; and
    sending, by the computer analysis system, a signal to the tool based on a determination that the calculated slope meets the threshold, the signal instructing the tool to terminate the process.

2. The method of claim 1, wherein the threshold is a user defined slope or a range within the user defined slope, wherein the slope represents a change in the intensity of the at least one reflected light calculated from the graphical representation.

3. The method of claim 1, further comprising storing a current time.

4. The method of claim 1, further comprising:
displaying the graphical representation of the data as a function of time, wherein the graphical representation provides a visual indication that the user defined threshold is met and represents the measured intensity of the at least one reflected light using a y-axis and represents time using an x-axis.

5. The method of claim 4, wherein the y-axis is in units of Lumens, and the x-axis is in units of seconds or milliseconds.

6. The method of claim 1, further comprising:
receiving user input that defines a frequency for the detector to measure the intensity for the at least one reflected light.

7. The method of claim 1, wherein the graphical representation is displayed using at least one of: a personal computer display, and a personal digital assistant display.

8. The method of claim 1, wherein the graphical representation is a line graph.

9. The method of claim 8, wherein the graphical representation includes an average line graph to represent an average of the line graph.

10. The method of claim 9, wherein a change in a slope of at least one of: the line graph and average line graph, indicates the transition between the dielectric anti-reflective coating film layer and the adjacent low-k film layer.

11. The method of claim 9, further comprising:
determining at least one of: a derivative of the line graph, and a derivative of the average line graph; and
plotting the at least one of: the derivative of the line graph, and the derivative of the average line graph, against time; and
displaying the plot to yield numerical values to represent a delta in the measured intensities of the at least one reflected light at any time.

12. A system comprising:
a user input device to facilitate user input defining a threshold to indicate a transition between a dielectric anti-reflective coating film layer and an adjacent low-k film layer;
a timer coupled to the input device to be initialized by a processor for time to commence at an initial value corresponding to a time of a tool starting a process;
a detector, coupled to the input device, to measure an intensity of at least one reflected light for at least two points in time;
memory to store the data measured by the detector of the intensity of the at least one reflected light for at least two points in time; and
a data processor coupled to the timer to initialize the timer, and coupled to the memory to plot a graphical representation of the stored data as a function of time, to determine whether a slope calculated from the graphical representation meets the threshold, and to send a signal to the tool based on a determination that the calculated slope meets the threshold, the signal instructing the tool to terminate the process.

13. The system of claim 12, wherein the threshold a user defined slope or a range within the user defined slope, wherein the slope represents a change in the intensity of the at least one reflected light calculated from the graphical representation.

14. The system of claim 12, wherein the memory is further to store a current time.

15. The system of claim 12, further comprising:
a display, coupled to the data processor, to display the graphical representation of the data as a function of time, wherein the graphical representation provides a visual indication that the user defined threshold is met and represents the measured intensity of the at least one reflected light using a y-axis and represents time using an x-axis.

16. The system of claim 15, wherein the y-axis is in units of Lumens, and the x-axis is in units of seconds or milliseconds.

17. The system of claim 15, wherein the display is at least one of: a personal computer display, and a personal digital assistant display.

18. The system of claim 12, wherein the user input device is to further facilitate user input defining a frequency for the detector to measure the intensity for the at least one reflected light.

19. The system of claim 12, wherein the graphical representation comprises at least one of: a line graph, and an average line graph to represent an average of the line graph.

20. The system of claim 19, wherein a change in a slope of at least one of: the line graph and average line graph, indicates the transition between the dielectric anti-reflective coating film layer and the adjacent low-k film layer.

21. The system of claim 19, further comprising:
determining at least one of: a derivative of the line graph, and a derivative of the average line graph; and
plotting the at least one of: the derivative of the line graph, and the derivative of the average line graph, against time; and
displaying the plot to yield numerical values to represent a delta in the measured intensities of the at least one reflected light at any time.

22. A computer readable medium comprising executable instructions which when executed on a processing system cause said processing system to perform a set of operations comprising:
receiving a user input, wherein the user input defines a threshold to indicate a transition between a dielectric anti-reflective coating film layer and an adjacent low-k film layer;
initializing a timer for time to commence at an initial value corresponding to a time of a tool starting a process;
receiving data from a detector, the data comprising an intensity of at least one reflected light that is measured by the detector for at least two points in time;
storing the data from the detector in memory;
plotting a graphical representation of the data as a function of time using the stored data;
determining whether a slope calculated from the graphical representation meets the threshold; and
sending a signal to the tool based on a determination that the calculated slope meets the threshold, the signal instructing the tool to terminate the process.

23. A system comprising:
means for receiving a user input, wherein the user input defines a threshold to indicate a transition between a dielectric anti-reflective coating film layer and an adjacent low-k film layer;
means for initializing a timer for time to commence at an initial value corresponding to a time of a tool starting a process;
means for receiving data from a detector, the data comprising an intensity of at least one reflected light for at least two points in time;

means for storing the data from the detector;
means for plotting a graphical representation of the data as a function of time using the stored data;
means for determining whether a slope calculated from the graphical representation meets the threshold; and
means for sending a signal to the tool based on a determination that the calculated slope meets the threshold, the signal instructing the tool to terminate the process.

* * * * *